United States Patent [19]
Pipino

[11] Patent Number: 5,835,231
[45] Date of Patent: Nov. 10, 1998

[54] BROAD BAND INTRA-CAVITY TOTAL REFLECTION CHEMICAL SENSOR

[75] Inventor: Andrew C. R. Pipino, Gaithersburg, Md.

[73] Assignee: The United States of America as represented by the Secretary of Commerce, Washington, D.C.

[21] Appl. No.: 962,171

[22] Filed: Oct. 31, 1997

[51] Int. Cl.[6] .................................................. G01N 21/31
[52] U.S. Cl. ........................... 356/440; 356/436; 356/437
[58] Field of Search ..................................... 356/436, 437, 356/440

[56] References Cited

U.S. PATENT DOCUMENTS

| 4,571,085 | 2/1986 | Anderson | 356/445 |
| 4,793,709 | 12/1988 | Jabar et al. | 356/445 |
| 5,437,840 | 8/1995 | King et al. | 356/346 X |

*Primary Examiner*—Vincent P. McGraw
*Attorney, Agent, or Firm*—Larson & Taylor

[57] ABSTRACT

A broadband, ultrahigh-sensitivity chemical sensor is provided that allows detection through utilization of a small, extremely low-loss, monolithic optical cavity. The cavity is fabricated from highly transparent optical material in the shape of a regular polygon with one or more convex facets to form a stable resonator for ray trajectories sustained by total internal reflection. Optical radiation enters and exits the monolithic cavity by photon tunneling in which two totally reflecting surfaces are brought into close proximity. In the presence of absorbing material, the loss per pass is increased since the evanescent waves that exist exterior to the cavity at points where the circulating pulse is totally reflected, are absorbed. The decay rate of an injected pulse is determined by coupling out an infinitesimal fraction of the pulse to produce an intensity-versus-time decay curve. Since the change in the decay rate resulting from absorption is inversely proportional to the magnitude of absorption, a quantitative sensor of concentration or absorption cross-section with 1 part-per-million/pass or better sensitivity is obtained. The broadband nature of total internal reflection permits a single device to be used over a broad wavelength range. The absorption spectrum of the surrounding medium can thereby be obtained as a measurement of inverse decay time as a function of wavelength.

14 Claims, 1 Drawing Sheet

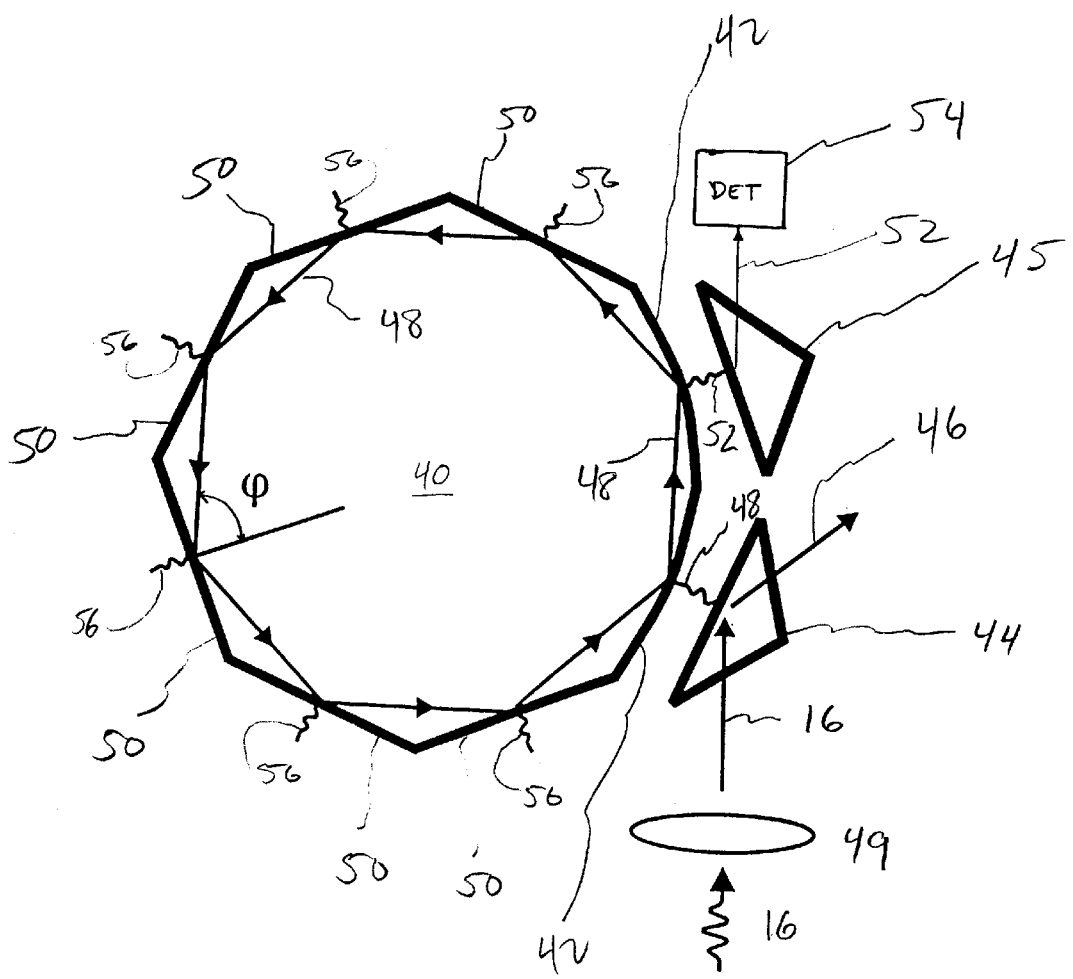

BROAD BAND INTRA-CAVITY TOTAL REFLECTION CHEMICAL SENSOR

FIELD OF THE INVENTION

The present invention relates to matter identifying devices, and more particularly, to a device for measuring the optical absorption by matter through the use of an evanescent wave generated by total internal reflection within a high-quality cavity.

BACKGROUND OF THE INVENTION

Optical absorption spectroscopy is fundamentally important in chemical analysis, providing decisive quantitative and qualitative information. Such diagnostic capabilities find substantial utility in both research and industrial process environments. Therefore, an advancement in sensitivity, accuracy, or adaptability of the technique will have a significant impact.

Absorption is usually determined from measurement of a ratio of optical powers at a certain wavelength. Recently, a new technique, termed cavity ring-down spectroscopy (E. K. Wilson, C&E News, Feb. 19, 1996, p. 34, incorporated herein by reference), has been developed to determine absorption by gases, which utilizes a pulsed light source and an optical cavity. Typically, light from a laser source is injected into a cavity which is formed by two high-reflectivity mirrors. The lifetime of the pulse in the cavity is highly sensitive to cavity losses, including absorption by gases. Measurement of the pulse decay time or "ring-down" time in the cavity can thereby provide a direct measure of absorption. Cavity ring-down eliminates the adverse effects of light source fluctuation, since the measurement is acquired with a single pulse of light. The feasibility of this technique arises from recent technological advances in optical polishing, which permit the fabrication of extremely low-scatter-loss optics. If ordinary optics such as high-reflectivity mirrors (R~99%) are used, the pulse lifetime in the cavity is too short for the cavity ring-down strategy to provide a significant improvement in sensitivity, as compared to conventional absorption methods. However, with the advent of superpolishing, such as that described in N. J. Brown, Ann. Rev. Mater. Sci. 16, p. 371 (1986), incorporated herein by reference, mirrors with 99.99% reflectivity or better can be fabricated to construct low-loss optical cavities, thereby permitting ultra-high sensitivity to be routinely realized. The cavity ring-down technique has thereby become a viable form of optical absorption metrology, with trace analysis capabilities that greatly exceed conventional absorption methods.

In its present form, the cavity ring-down technique has severe limitations. In particular, the high reflectivities required to form sufficiently low-loss cavities are typically achievable only for narrow wavelength bands (~50 nm), using multilayer dielectric coatings over superpolished substrates. Separate sets of mirrors are therefore required to cover a modest wavelength range, which increases expense and greatly limits the extent of information acquired per experiment. In their present form, cavity ring-down spectrometers are also moderately large in physical size, with cavities ranging in length from 0.1 to 2 meters. The long cavity length is, in part, required to achieve a high density of longitudinal cavity modes. These cavity modes, which arise from the use of a standing wave cavity, must be sufficiently dense to accurately sample the absorption spectrum of the gas. Furthermore, cavity ring-down has only been applied to gas phase measurements, due largely to the higher cavity losses associated with condensed matter sampling. The elimination of these restrictions would greatly increase the range of application and therefore facilitate proliferation of the cavity ring-down technique. Indeed, the development of a small, broadband cavity ring-down spectrometer, which permits all states of matter to be probed, would extend absorption spectroscopy into previously unrealizable regimes of trace analysis.

SUMMARY OF THE INVENTION

In accordance with the invention, a device is provided which permits broadband, ultrahigh-sensitivity chemical detection through utilization of a small, extremely low-loss, monolithic optical cavity. The cavity is fabricated from highly transparent optical material (e.g., in the shape of a regular polygon with one or more convex facets) to form a stable resonator for ray trajectories sustained by total internal reflection. Optical radiation enters and exits the monolithic cavity by photon tunneling in which two totally reflecting surfaces are brought into close proximity. Since the loss per pass is small when no absorbing material is in contact with the cavity, an injected pulse circulates for a large multiple of the round trip time. In the presence of absorbing material, the loss per pass is increased since the evanescent waves, that exist exterior to the cavity at points where the circulating pulse is totally reflected, are absorbed. The decay rate of an injected pulse is determined by coupling out a small fraction of the circulating energy to produce an intensity-versus-time decay curve. Since the change in the decay rate resulting from absorption is inversely proportional to the magnitude of absorption, a quantitative sensor of concentration or absorption cross-section with 1 part-per-million/pass or better sensitivity is obtained. The broadband nature of total internal reflection permits a single device to be used over a broad wavelength range. The absorption spectrum of the surrounding medium can thereby be obtained as a measurement of inverse decay time as a function of wavelength. The device can be miniaturized and combined with fiber optic input and output coupling to provide a convenient probe of remote, hazardous, or in vivo environments.

As will be apparent, the invention achieves broadband, ultrahigh sensitivity measurement of optical absorption for any state of matter by cavity ring-down, through use of a small, monolithic, total internal reflection ring cavity device. The broadband character of the device arises from the nature of total internal reflection, which is used to sustain trajectories within the monolithic cavity. The device can probe any state of matter through the use of evanescent waves, which exist external to the cavity at points where the internally circulating pulse is totally reflected. The evanescent waves decay exponentially in space, providing a well-defined sample path length for absorbing matter, without introducing any additional cavity losses. The device of the invention represents a major advance in absorption measurement technology, which fully resolves the above-mentioned limitations of the cavity ring-down technique.

In accordance with a preferred embodiment of the invention, an intra-cavity total reflection apparatus is provided for high sensitivity measurement of the optical absorption of a test material. The apparatus includes: an injecting means for producing light for a predetermined length of time; a closed stable optical cavity, comprising an internal total reflecting surface, for receiving the light within the cavity and for providing total internal reflection of the light at the internal surface so as to generate a plurality of evanescent waves which emanate from the cavity at spaced points and which decay within a length outside of said cavity beyond the surface, the test material being disposed outside of the cavity within the decay length of one or more of the evanescent waves; and a measuring means for monitoring the circulating light to determine the decay time of the light.

Preferably, the cavity has one of a polygonal, spherical, cylindrical or toroidal shape. In a preferred embodiment, the internal surface further includes an input convex interfacing facet for receiving the light and an output convex interfacing facet through which one of the evanescent waves is transmitted to the measuring means. In an even more preferred embodiment, the input and output convex interfacing facets have a radius of curvature that is dependent on the size of the cavity.

In an advantageous embodiment, the injecting means includes at least one lens for transverse mode matching the light. The cavity is preferably made of fused silica, and an output coupling means, such as a prism, a waveguide or an optical fiber is used to couple light into and out of the cavity.

In an alternative embodiment, the circulating light in the cavity is monitored by detecting scattered light which radiates from the cavity.

In accordance with another aspect of the invention, a method of high sensitivity measurement of the optical absorption of a test material is provided, the method includes the steps of: injecting light having a predetermined duration by way of photon tunnelling through a surface of a closed polygonal shaped stable optical cavity having multiple reflecting facets forming the surface so that the light circulates within the optical cavity off of the facets and generates a plurality of evanescent waves which decay within a decay length outside of the optical cavity beyond the surface; disposing the test material outside of the cavity within the decay length of one of the evanescent waves so as to affect the decay time taken by the light to decay within the cavity; and measuring the light intensity of the circulating light to determine the decay time of said light.

Other features and advantages of the invention will be set forth in, or apparent from, the following detailed description of the preferred embodiments of the invention.

BRIEF DESCRIPTION OF THE DRAWINGS

The single figure in the drawings is a schematic top elevational view of a monolithic optical cavity apparatus in accordance with a preferred embodiment of the invention.

DETAILED DESCRIPTION OF THE PREFERRED EMBODIMENTS

A further preliminary discussion is thought to be helpful at this point in fully understanding the invention. The measurement of optical absorption is fundamental to science and engineering, since an absorption spectrum provides a fingerprint which permits the qualitative and quantitative analysis of material composition. Absorption measurements are also frequently used to extract rates of chemical reactions and other processes. Key objectives in the development of a new technology for measurement of absorption are: 1) a reduction of the minimum detectable concentration, 2) an increase in the spatial resolution of the measurement, and 3) the incorporation of tunable, powerful, and highly monochromatic laser sources. By reducing the detection limit, important chemical reactions and processes that involve trace quantities or very short path lengths will be, in some cases, detectable for the first time or examined with higher signal-to-noise ratio thereby allowing more reliable quantification.

Previous attempts to increase the limit of detection have typically increased the sampled path length, which inherently results in a decrease in spatial resolution. A few devices have been developed which permit multiple sampling of a specific region, but typically with a small number of passes and a large beam diameter. The device of the present invention which uses a multiple-pass geometry with refocussing, substantially improves sensitivity and spatial resolution. Furthermore, by using a laser source with the device of the invention, the spatially coherent nature of laser light permits greater spatial resolution, since a focal spot size limited only by diffraction can be readily achieved. The laser-based device also benefits from the high output power and broad wavelength range obtainable through the combination of tunable, pulsed dye lasers and harmonic generation. Considering the current technological trend toward the micro- and nanostructured domains, the development of a sensitive absorption device with high-spatial resolution will likely facilitate technological innovations.

To permit utilization of pulsed laser sources, the device circumvents the complications of pulse-to-pulse fluctuation, which is characteristic of pulsed laser systems. This is achieved since a measurement is accomplished with a single pulse not by comparison of, for example, a sample end reference channel using two different light beams.

In the case of Attenuated Total Reflection (ATR) developed extensively by Harrick, *Internal Reflection Spectroscopy*, by N. J. Harrick (*Interscience Publishers*, New York 1967), incorporated herein by reference, an evanescent wave is generated by internal reflection in an optical cavity such as a prism, plate or thin-film waveguide at an internal angle of incidence that exceeds the critical angle. In ATR spectroscopy, the evanescent wave generated by total internal reflection at the base of a prism is used for optical absorption measurements by the conventional optical power ratio method. Absorption is determined from the optical power loss incurred in the critically reflected beam relative to total reflection when no absorbing material is present in the evanescent wave region.

ATR can be used to measure absorption for samples in the solid, liquid or gas phases, but is also highly effective for probing powders, fibers, thin-films, and absorbed molecular monolayers. For studies of thin-films and monolayers, ATR benefits from the enhanced surface electric field which exists at the interface where total reflection occurs. The direction of the surface field can also be controlled through polarization selection to probe molecular orientation effects, which can be important in, for example, catalysis and adhesion.

In optical cavity ATR, a light beam is coupled into a mode of an optical cavity, which contains an evanescent wave component that decays exponentially outside of the waveguide. Absorbing material within the decay length is then probed by measuring a corresponding power loss in the out-coupled beam after traversing the waveguide for a predetermined distance.

Waveguide cavity ATR has the advantage over ordinary ATR of increased effective path length, since light rays coupled into the cavity experience a large number of internal reflections over a short distance. The effective path length is proportional to the product of the total number of reflections and the evanescent wave decay length. However, conventional waveguide cavity ATR still employs an optical power ratio measurement, which ultimately limits its utility in trace analysis. In contrast, use of the monolithic, total internal reflection cavity in a cavity ring-down device like that shown in the figure discussed below eliminates the effect of source fluctuation, while achieving long effective path lengths through repeated circulation in addition to multiple reflections.

Although optical cavities have been described in many patents and publications, this does not detract from the originality of novel applications of such technology. For example, laser resonators and spectrum analyzers are common implementations of optical cavities, which in some cases use identical cavity designs. Monolithic cavities, in which the cavity is fabricated entirely from a single block of material, can utilize multilayer coatings, a combination of coatings with total reflection, or complete total internal reflection with photon tunneling for input/output. Monolithic cavities utilizing total reflection have been used as laser resonators, nonlinear conversion devices, and spectrum analyzers as described in *S. Schiller, I.I. Yu, M. M. Fejer, and R.L. Byer, Opt. Lett.* 17, p. 378 (1992); *K. Fiedler, S. Schiller, R. Paschotta, P. Kurz, J Mlynek, Opt. Lett.* 18, p. 1786 (1993); and *Schiller, M. M. Jejer, A. Sizmann, R. L. Byer*, U.S. Pat. No. 5,227,911, all of which are incorporated herein by reference. In the case of monolithic resonators or nonlinear conversion devices, the gain or conversion medium is the cavity material itself. In the case of spectrum analyzers, the cavity is typically used for frequency analysis of an input laser beam based on the beam's resonate interaction with the cavity modes. These implementations are distinctly different from devices that are designed to measure the optical absorption spectrum of a material.

Apart from ATR is the cavity ring-down spectroscopy (CRDS) technique described in *A. O'Keefe and D. A. G. Deacon, Rev. Sci Instrum.* 59, p. 2544 (1988) incorporated herein by reference, which is used for measuring the optical absorption spectra of gases. This technique was originally applied to narrowband gas phase absorption spectroscopy. U.S. Pat. No. 5,313,270 to Fishman and Haar, incorporated herein by reference, describes essentially identical technology to that of the O'Keefe reference mentioned above, with an intended application to the measurement of mirror reflectivity.

In CRDS, a single laser pulse is injected into a high-Q optical cavity, typically comprising a pair of concave high-reflectivity mirrors. Since the cavity Q-factor is high, the pulse makes many round trips, incurring only a small loss in amplitude per pass due to small intrinsic cavity losses resulting from, for example, mirror surface roughness scattering. Typically, the cavity is enclosed in a chamber which is filled with a gas of interest. When the frequency of the injected pulse corresponds to a resonant transition of the gas, the pulse amplitude loss per pass directly reflects the magnitude of the absorption. The temporal decay of the injected pulse is determined by monitoring the weak transmission which escapes from the cavity through one of the high-reflectivity mirrors. The transmitted intensity decays exponentially at a rate which reflects the total cavity losses, including absorption losses. Measurement of absorption is thereby achieved through a measurement of decay time instead of through a ratio of optical intensities. This time based measurement is equivalent to a large number of power ratio measurements with the same laser pulse, which inherently improves the accuracy and precision of the measurement since use of a single pulse eliminates the adverse effects of pulse-to-pulse fluctuation.

CRDS has only been applied to gas phase measurements, since the use of condensed matter sampling schemes which are common to transmission measurements, result in substantial intrinsic cavity losses which degrade the system performance. However, by utilizing intra-cavity total reflection, the advantages of a time-based absorption measurement can be combined with the advantages of ATR. The net result is a novel strategy for measurement of optical absorption by all states of matter. This strategy is fundamentally different from ATR, since a measurement of time instead of a ratio of intensities, is utilized. This strategy is different from CRDS since condensed matter can be probed through generation of an evanescent wave. Furthermore, the highly-localized nature of the evanescent wave combined with the spatial coherence provided by a laser source permits diffraction-limited spatial resolution through actuation of a selected mode or set of modes and provides a decisively defined sample path length, which is necessary for accurate quantitative measurements.

The embodiment illustrated in the drawing circumvents narrowband restrictions, and maintains applicability to all states of matter, and also permits miniaturization of the device. For example, the entire structure can be fabricated on a semiconductor substrate using well known integrated circuit technology.

The embodiment shown in the drawing illustrates a possible cavity design. In general, a cavity 40 is shown which takes the form of a regular, planar polygon having one or more facts and two slightly convex facets 42 and 43 that are typically adjacent, respectively, to an input coupling means 44 and an output coupling means 45, both means being shown here as prisms. Convex surface 42 is required to form a stable optical cavity for internal ray trajectories. The choice of radius of curvature for the convex surfaces 42 and 43 depends on the size of the cavity 40. Coupling means 44 and 45 permit optical radiation to enter and exit the cavity by a photon tunneling mechanism, which is also termed frustrated total reflection (FTR) in *IN. Court and F. K. Von Willisen, Appl. Opt.* 3, p. 719 (1964) which is incorporated herein by reference. The extent of coupling provided by coupling means 44 and 45 depends on the distance between the coupling means and the cavity 40 and is a well-understood and characterized function. The figure shows the use of two coupling means to provide separate locations for entering and exiting rays, although a single element such as input coupling means 44 could be used for both purposes. The incoming light 16 is directed onto the input coupling means 44 with an angle of incidence at the base of the input coupling means 44 which exceeds the critical angle so that total reflection occurs, producing a reflected pulse 46. Through photon tunneling, a pulse 48, which is a small fraction of the incident pulse, is injected into the cavity 40. A lens 49 is selected to traverse mode match the injected pulse 48 to the cavity according to the principals discussed in *H. Kogelnik, Bell System Tech. Journal, Mar.* 1965, p. 455, which is incorporated herein by reference.

The injected pulse 48 is appropriately directed to establish a stable trajectory so as to circulate around the cavity to be totally reflected by all encountered planar surfaces 50 and convex surfaces 42. The loss per round-trip for the circulating injected pulse 48 can be made very small by super-polishing all facet surfaces 50, 42 and 43, and by fabricating the cavity 40 from highly transmissive material. The loss per surfaces 50, 42 and 43, arising from surface roughness scattering, can be estimated from equation (1) below which is discussed in detail in *H. Hogrefe and C. Kunz, Appl. Opt.* 26, p. 2851 (1987) and incorporated herein by reference.

$$1 - R = \left( \frac{4\pi\sigma\cos\Theta}{\lambda} \right)^2 \tag{1}$$

In equation (1), R is the effective reflectivity of the surface, $\lambda$ is the wavelength, $\sigma$ is the root-mean-square (RMS)

surface roughness, and Θ is the angle of incidence. For a 0.1 nm RMS surface, which is well within the current capabilities of polishing technology, effective mirror reflectivities of 99.9999% are possible, reducing the loss per surface to only a few parts-per-million (ppm).

The total loss of power incurred per round trip of injected pulse 48 through the cavity 40 is approximately the sum of the losses from surface scattering, bulk cavity material absorption and absorption by the material to be measured. Through a judicious selection of cavity material, bulk losses can also be minimized. For example, fiber optical grade fused silica can have absorption losses of less than 1 db/km, which for devices with dimensions on the order of a centimeter, allows a light to circulate in the monolithic cavity 40 of the drawing for greater than 100,000 round trips within the pulse decay time. This pulse decay time is also known as ring down time and is further explained in the O'Keefe reference referred to above. A small fraction of the circulating injected pulse 48 is sampled by the output coupling means 45 to monitor the decay rate of the circulating injected pulse 48. The degree of output coupling is designed to be small to minimize total cavity losses, yet the output coupled radiation pulse 52 is of sufficient intensity to permit detection with a common detector 54, such as a photomultiplier tube. If a single element was used for both input coupling and output coupling as described above (i.e., coupling means 44), detector 54 would be repositioned to receive the outcoupled fraction of pulse 48 that would then be coincident with pulse 46; pulse 46 then being separated from the outcoupled fraction by methods well understood by those of ordinary skill in the art. By monitoring with detector 54, the output coupled pulse 52 as a function of time over the circulating pulse lifetime, a decay curve is obtained which is characteristic of the total cavity losses. Since the intrinsic cavity losses are fixed by the cavity design and fabrication process, additional losses incurred due to absorption of evanescent wave 56 introduced by material present at facets 50 will be directly probed by determining changes in the decay rate of an output signal corresponding to the output coupled light 52.

The principles and applications of evanescent waves in ATR absorption spectroscopy including the relationship between sensitivity, evanescent wave decay length, angle of incidence, and refractive index difference across the totally reflecting boundary are further described in *Internal Reflection Spectroscopy*, by N. J. Harrick (*Interscience Publishers*, New York 1967) which was referred to above. The methods of ATR, including techniques for analysis of gases, liquids, solids, powders and thin films are directly applicable to diagnostics with the present invention. The mean angle of incidence for the totally reflected injected pulse 48 is determined by the choice of cavity geometry, which for an N sided regular polygon is given by, $$\phi = \frac{\pi}{2}\left(1 - \frac{2}{N}\right) \quad (2)$$

The angle of incidence for all stable rays in the cavity 40 must exceed the critical angle given by, $$\theta_c = \text{SIN}^{-1}\left(\frac{n_2}{n_1}\right) \quad (3)$$

where the material composing cavity 40 is specified as medium $n_1$ and the medium to be measured which is surrounding the cavity is $n_2$. Sensitivity can be optimized for particular analysis conditions through the choice of angle of incidence and cavity material in accordance with methods of ATR. Polarization dependent spectroscopy is also feasible, similar to ATR.

In summary, the monolithic, total internal reflection ring-cavity sensor described in the embodiment illustrated in the drawing represents a major advance in absorption measurement technology that surpasses existing absorption methods to reach a performance level previously attained only by less direct methods, such as fluorescence. The device circumvents essentially all of the previously encountered limitations of the cavity ring-down technique thereby permitting broad extension of the method into new domains of application. Specifically, the monolithic, ring-cavity approach allows broadband cavity ring-down spectroscopy of solids, liquids, gases, and thin films with ultra-high sensitivity by a miniaturizable device. This technology supplants the previous technology that suffered from narrow bandwidth, large physical size, and ease of application only to gases. Furthermore, the monolithic, ring-cavity device can potentially be combined with fiber optic input- and output-coupling to probe many otherwise inaccessible environments.

This embodiment in the drawing can alternatively utilize pulsed, dye lasers or CW lasers including diode lasers as a source for frequency scanning. Also, picosecond or femtosecond pulsed laser sources with continuum generation, followed by frequency analysis of the output signal by either interferometry or dispersion methods can be implemented. Furthermore, it is possible to vary input/output coupling through the control of the coupler-to-cavity distance, through, for example, the use of piezoelectric translators. Alternatively, one can fix input or output coupling through the use of a spacer layer or air gap. Another option is to utilize fiber optic input/output coupling such that the cavity can be positioned remotely from the source and detection system. Another embodiment uses cavity materials other than fused silica to allow spectral regions where fused silica absorbs to be probed. In addition to the monolithic polygons described above, other monolithic structures could be utilized, such as a sphere, a cylinder, or a fiber formed, for example, by a piece of fiber optic cable whose ends are joined to form a toroid. In any embodiment, a non-planar ring cavity could be used or the invention could be implemented in micro-optics.

Anticipated commercial applications for the invention include:

1. Biosensor applications
2. Catalysis
3. Corrosion
4. Adhesion
5. Trace analysis
6. Capillary electrophoresis detector
7. Process measurements
8. Optical constant determinations
9. Hostile environments
10. Trace analysis in general
11. Research tool for surface science research Although the present invention has been described to specific exemplary embodiments thereof, it will be understood by those skilled in the art that variations in modifications can be effected in these exemplary embodiments without departing from the scope and spirit of the invention.

We claim:

1. An intra-cavity total reflection apparatus for high sensitivity measurement of the optical absorption of a test material, said apparatus comprising:

injecting means for producing light for a predetermined length of time;

a closed stable optical cavity, comprising an internal total reflecting surface, for receiving said light within said cavity and for providing total internal reflection of said light at said internal surface so as to generate a plurality of evanescent waves which escape from said cavity at spaced points and which decay within a length outside of said cavity beyond said surface, said test material being disposed outside of said cavity within the decay length of one of said evanescent waves; and measuring means for monitoring one of said evanescent waves to determine the decay time of said light.

2. An apparatus as claimed in claim 1, wherein said closed stable optical cavity has one of a polygonal, spherical, cylindrical or toroidal shape.

3. An apparatus as claimed in claim 2, wherein said surface further comprises an input convex interfacing facet for receiving said light and an output convex interfacing facet through which one of said evanescent waves is transmitted to said measuring means.

4. An apparatus as claimed in claim 3, wherein said input and output convex interfacing facets have a radius of curvature that is dependent on the size of said cavity.

5. An apparatus as claimed in claim 3, wherein said injecting means includes at least one lens for transverse mode matching said light.

6. An apparatus as claimed in claim 1 wherein said cavity is comprised of fused silica.

7. An intra-cavity total reflection apparatus for high sensitivity measurement of the optical absorption of a test material, said apparatus comprising:

injecting means for producing light for a predetermined length of time;

input coupling means for receiving said light and transmitting a portion of said light;

a polygonal shaped stable optical cavity, comprising a total reflecting internal surface including an input convex interfacing facet, for receiving at said input convex interfacing facet said light portion by way of photon tunnelling and for providing total internal reflection of said light portion at said surface within said cavity while generating a plurality of evanescent waves which escape from said cavity at spaced points and which decay within a length outside of said cavity, said test material being disposed outside of said cavity within the decay length of one of said evanescent waves; and measuring means for monitoring one of said evanescent waves to determine the decay time of said light portion.

8. An apparatus as claimed in claim 7, wherein said surface further comprises an output convex interfacing facet through which one of said evanescent waves is transmitted to said measuring means.

9. An apparatus according to claim 8, further comprising an output coupling means disposed between said output convex interfacing facet and said measuring means.

10. An apparatus as claimed in claim 9, wherein said input and output convex interfacing facets have a radius of curvature that is dependent on the size of said cavity.

11. An apparatus as claimed in claim 9, said input coupling means includes a lens for transverse mode matching said light.

12. An apparatus as claimed in claim 9, wherein each of said input and output coupling means each comprises one of a piezoelectric translator, a fiber optic coupling, a prism and a wave guide.

13. An apparatus as claimed in claim 7 wherein said cavity is comprised of fused silica.

14. A method of high sensitivity measuring the optical absorption of a test material, said method comprising the steps of:

injecting light having a predetermined duration by way of photon tunnelling through a surface of a closed polygonal stable shaped optical cavity having multiple reflecting facets forming said surface so that said light circulates within said optical cavity off of said facets and generates a plurality of evanescent waves which decay within a decay length outside of said optical cavity beyond said surface;

disposing said test material outside of said cavity within said decay length of one of said evanescent waves so as to affect the decay time taken by said light to decay within said cavity; and measuring one of said evanescent waves to determine the decay time of said light.

* * * * *